United States Patent
Cohen et al.

(10) Patent No.: US 12,102,702 B2
(45) Date of Patent: Oct. 1, 2024

(54) PERSONAL CARE COMPOSITIONS

(71) Applicant: Colgate-Palmolive Company, New York, NY (US)

(72) Inventors: Aaron Cohen, New Brunswick, NJ (US); Ningwei Li, Highland Park, NJ (US); Junhong Mao, Plainsboro, NJ (US); Hongwei Shen, Holmdel, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/743,262

(22) Filed: May 12, 2022

(65) Prior Publication Data

US 2022/0370319 A1    Nov. 24, 2022

Related U.S. Application Data

(60) Provisional application No. 63/188,750, filed on May 14, 2021.

(51) Int. Cl.

| | | |
|---|---|---|
| *A61K 8/44* | (2006.01) | |
| *A61K 8/42* | (2006.01) | |
| *A61K 8/49* | (2006.01) | |
| *A61K 8/60* | (2006.01) | |
| *A61K 8/67* | (2006.01) | |
| *A61Q 5/02* | (2006.01) | |
| *A61Q 5/12* | (2006.01) | |
| *A61Q 19/10* | (2006.01) | |

(52) U.S. Cl.
CPC ............... *A61K 8/44* (2013.01); *A61K 8/498* (2013.01); *A61K 8/604* (2013.01); *A61K 8/67* (2013.01); *A61K 8/671* (2013.01); *A61K 8/673* (2013.01); *A61K 8/676* (2013.01); *A61K 8/678* (2013.01); *A61Q 5/02* (2013.01); *A61Q 5/12* (2013.01); *A61Q 19/10* (2013.01); *A61K 8/42* (2013.01); *A61K 8/442* (2013.01)

(58) Field of Classification Search
None
See application file for complete search history.

(56) References Cited

U.S. PATENT DOCUMENTS

| | | | |
|---|---|---|---|
| 6,818,204 B2 | 11/2004 | Lapidus | |
| 9,271,908 B2 | 3/2016 | Allef et al. | |
| 9,409,853 B2 | 8/2016 | Schuch et al. | |
| 9,987,207 B1 | 6/2018 | Wang et al. | |
| 10,328,005 B2 | 6/2019 | Carnali | |
| 2015/0010487 A1* | 1/2015 | Snyder ................ | A61K 8/893 424/70.122 |
| 2022/0304910 A1* | 9/2022 | Scheidler-Foegle ..... | A61K 8/44 |

FOREIGN PATENT DOCUMENTS

| | | |
|---|---|---|
| CN | 103961285 | 8/2014 |
| CN | 104940096 | 9/2015 |
| CN | 105902420 | 8/2016 |
| CN | 106726634 | 5/2017 |
| DE | 4428823 | 2/1996 |
| EP | 2786742 | 10/2014 |
| FR | 3005574 | 11/2014 |
| WO | 2008/110942 | 9/2008 |
| WO | WO-2022184859 A1 * | 9/2022 ........... A61K 8/9789 |

OTHER PUBLICATIONS

Cocoeco ("It's homemade Shampoo Day!", an internet article published on Jun. 14, 2019 and obtained from the website: https://cocoblog.ca/en/how-make-liquid-shampoo/#:~:text=You%20can%20substitute%20decyl%20glucoside,in%20many%20hair%20care%20products). (Year: 2019).*

Ishy ("Holifrog Superior Omega Nutritive Gel Wash ingredients (Explained)", a product sheet dated Apr. 23, 2021 and obtained from the Inci Decoder website: https://incidecoder.com/products/holifrog-superior-omega-nutritive-gel-wash ) (Year: 2021).*

English translation for WO 2022/184859 A1 (Year: 2022).*

A product advertisement for "Hemp Protein Powder 40" obtained at the website: https://britishhempco.com/products/hemp-flour (date unknown).*

International Search Report and the Written Opinion of the International Searching Authority issued in International Application PCT/US2022/029033 mailed Sep. 16, 2022.

* cited by examiner

*Primary Examiner* — Sin J Lee

(57) ABSTRACT

Disclosed are personal care compositions, e.g., skin care compositions, comprising an acyl glutamate, e.g., sodium cocoyl glutamate, in an amount of from 1% to 10% by weight of the composition and at least one topically active compound, wherein the at least one topically active compound comprises a vitamin, as well as to methods of using these compositions.

15 Claims, 4 Drawing Sheets

PERSONAL CARE COMPOSITIONS

CROSS-REFERENCE TO RELATED APPLICATIONS

This application claims the benefit of priority to U.S. Provisional Patent Application Ser. No. 63/188,750 filed May 14, 2021, the entirety of which is incorporated herein by reference.

BACKGROUND

Conventional personal care compositions primarily utilize anionic surfactants as a foaming agent. Sulfate-based surfactants are commonly used for personal care products such as shampoo, body wash and face cleanser. The most common sulfate-based surfactants are sodium lauryl sulfate (SLS) and sodium lauryl ether sulfate (SLES). However, consumer studies and surveys have shown that there is a desire to use personal care compositions that do not contain any sulfate-based surfactants, as some consumers experience relatively greater sensitivity to these ingredients. Sulfates can cause varying levels of skin and eye irritation, which may get worse the longer the product is in contact with the skin. Sulfate-free compositions are gaining more and more attraction among consumers, who associate sulfate-free products with more natural and less harsh materials.

Among other benefits, sulfate-free bases offer a unique opportunity to re-evaluate active delivery, in particular active deposition. In contrast to leave on products, active delivery from rinse off products like liquid soap or body wash is extremely challenging due to the limited time period during which the formula is in contact with the skin. There is a need for sulfate-free personal care compositions which effectively deposit topically active compounds on the skin.

BRIEF SUMMARY

In one aspect, the disclosure provides a personal care composition which comprises an acyl glutamate, e.g., sodium cocoyl glutamate (SCG), in an amount of from 1% to 10% by weight of the composition and at least one topically active compound, wherein the at least one topically active compound comprises a vitamin. In some embodiments, the acyl glutamate is $C_{8-25}$ acyl glutamate, e.g., $C_{8-18}$ acyl glutamate, $C_{10-18}$ acyl glutamate, or $C_{10-16}$ acyl glutamate. In some embodiments, the acyl glutamate is selected from dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and mixtures thereof. In certain embodiments, the acyl glutamate is cocoyl glutamate, e.g., sodium cocoyl glutamate. In some embodiments, the vitamin is vitamin E, e.g., vitamin E acetate. In some embodiments, the composition is free of sulfate. In some embodiments, the composition is a rinse off composition. In some embodiments, the composition is a liquid soap, liquid hand soap, shower gel, body wash, shampoo, or hair conditioner.

In some embodiments, the acyl glutamate is present in an amount of from 1% to 9%, e.g., from 1% to 8%, from 1% to 7%, from 1% to 6%, from 1% to 5%, from 1% to 4%, from 1% to 3%, or from 1% to 2%, by weight of the composition. In some embodiments, the acyl glutamate is present in an amount of from 1.5% to 10%, e.g., from 1.5% to 9%, from 1.5% to 8%, from 1.5% to 7%, from 1.5% to 6%, from 1.5% to 5%, from 1.5% to 4%, from 1.5% to 3%, or from 1.5% to 2%, by weight of the composition. In some embodiments, the acyl glutamate is present in an amount of from 2% to 10%, e.g., from 2% to 9%, from 2% to 8%, from 2% to 7%, from 2% to 6%, from 2% to 5%, from 2% to 4%, or from 2% to 3%, by weight of the composition. In some embodiments, the acyl glutamate is present in an amount of from 3% to 10%, e.g., from 3% to 9%, from 3% to 8%, from 3% to 7%, from 3% to 6%, from 3% to 5%, or from 3% to 4%, by weight of the composition. In some embodiments, the acyl glutamate is present in an amount of from 4% to 10%, e.g., from 4% to 9%, from 4% to 8%, from 4% to 7%, from 4% to 6%, or from 4% to 5%, by weight of the composition. In some embodiments, the acyl glutamate is present in an amount of from 5% to 10%, e.g., from 5% to 9%, from 5% to 8%, from 5% to 7%, or from 5% to 6%, by weight of the composition. In some embodiments, the acyl glutamate is present in an amount of from 6% to 10%, e.g., from 6% to 9%, from 6% to 8%, or from 6% to 7%, by weight of the composition. In some embodiments, the acyl glutamate is present in an amount of from 7% to 10%, e.g., from 7% to 9%, or from 7% to 8%, by weight of the composition. In some embodiments, the acyl glutamate is present in an amount of from 8% to 10%, e.g., from 8% to 9% or from 9% to 10%, by weight of the composition.

In some embodiments, the composition comprises a co-surfactant. In some embodiments, the co-surfactant comprises an alkyl glucoside. In some embodiments, the alkyl glucoside is present in an amount of from 1% to 9%, e.g., from 2% to 8%, from 2% to 7%, from 2% to 6%, from 2% 5%, from 2% to 4%, from 2% to 3%, from 3% to 8%, from 3% to 7%, from 3% to 6%, from 3% to 5%, from 3% to 4%, from 4% to 8%, from 4% to 7%, from 4% to 6%, from 4% to 5%, from 5% to 8%, from 5% to 7%, from 5% to 6%, from 6% to 8%, from 6% to 7%, or from 7% to 8%, by weight of the composition.

The alkyl glucoside may be $C_{8-25}$ alkyl glucoside, e.g., $C_{8-18}$ alkyl glucoside, or $C_{10-18}$ alkyl glucoside. In some embodiments, the alkyl glucoside is selected from decyl glucoside, caprylyl/capryl glucoside, lauryl glucoside, coco-glucoside, octyl glucoside, cetearyl glucoside, cetyl glucoside, hexadecyl glucoside, arachidyl glucoside, and a combination thereof. In some embodiments, the alkyl glucoside is selected from decyl glucoside, caprylyl/capryl glucoside and a combination thereof. In certain embodiments, the weight ratio of caprylyl/capryl glucoside to decyl glucoside present in the composition is about 3 to 1.

In another aspect, the disclosure provides a method of depositing a topically active compound on the skin, comprising applying an effective amount of any of personal care compositions as disclosed herein to the skin.

In another aspect, the disclosure provides the use of a surfactant system comprising an acyl glutamate, e.g., sodium cocoyl glutamate, in an amount of from 1% to 10% by weight of the composition in a personal care composition comprising at least one topically active compound, e.g., vitamin, e.g., vitamin E, for increasing the deposition of the at least one topically active compound on the skin when applying the composition to the skin. In some embodiments, the composition comprises an alkyl glucoside as a co-surfactant.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

Figure 1:
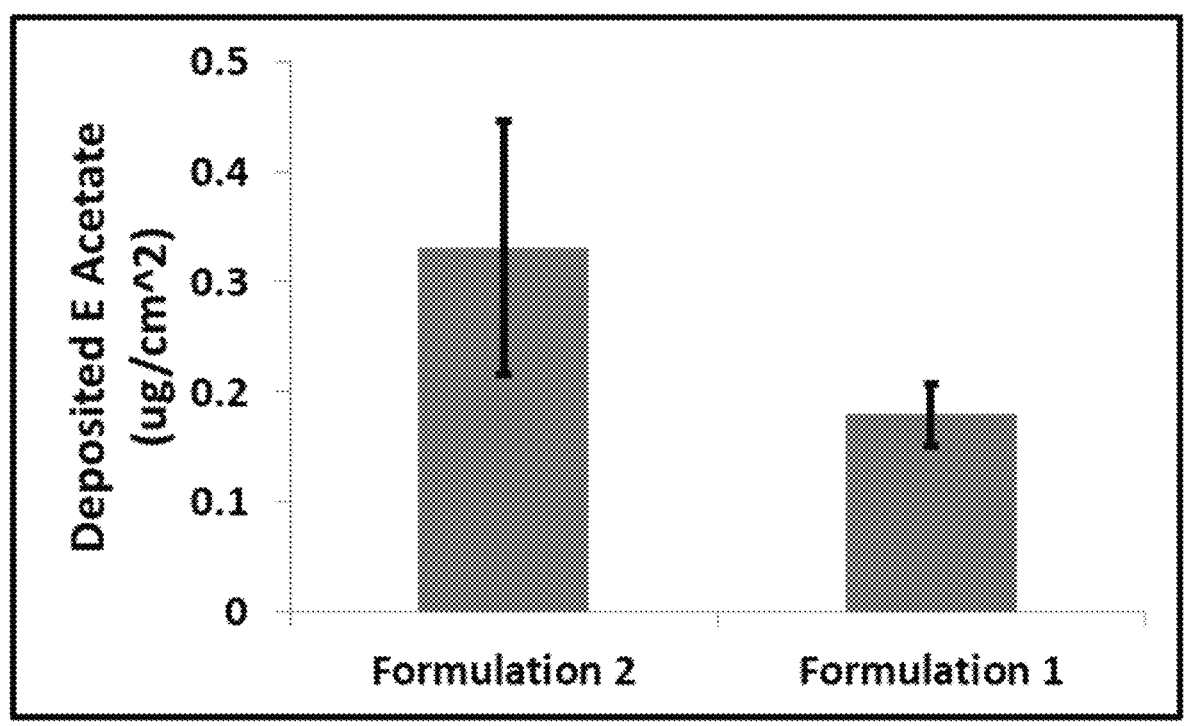
FIG. 1 shows vitamin E acetate deposition of Formulation 1 and Formulation 2.

The following description of various typical aspect(s) is merely exemplary in nature and is in no way intended to limit the disclosure, its application, or uses.

As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight. The amounts given are based on the active weight of the material.

The present disclosure relates to sulfate-free personal care compositions that effectively deposit topically active compounds (e.g., vitamin) on the skin. It has been found that the addition of sodium cocoyl glutamate (SCG), a mild anionic surfactant, into a liquid sulfate-free rinse off product leads to a dramatic increase in the deposition of vitamin E acetate when the composition is applied to the skin. Sodium cocoyl glutamate is a particularly appealing choice of surfactant as it is derived from plants and is milder than sulfate-based anionic surfactants.

The present disclosure provides, in an aspect, a personal care composition (Composition 1.0), e.g., skin care composition, comprising an acyl glutamate, e.g., sodium cocoyl glutamate, in an amount of from 1% to 10% by weight of the composition and at least one topically active compound, wherein the at least one topically active compound comprises a vitamin.

For example, the composition includes:

1.1. Composition 1.0, wherein the acyl glutamate is $C_{8-25}$ acyl glutamate, e.g., $C_{8-18}$ acyl glutamate, $C_{10-18}$ acyl glutamate, or $C_{10-16}$ acyl glutamate, optionally wherein the acyl glutamate is selected from dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and a combination thereof, preferably sodium cocoyl glutamate.

1.2. Any of the preceding compositions, the acyl glutamate is cocoyl glutamate, e.g., sodium cocoyl glutamate.

1.3. Any of the preceding compositions, wherein the acyl glutamate is present in an amount of from 1% to 9%, e.g., from 1% to 8%, from 1% to 7%, from 1% to 6%, from 1% to 5%, from 1% to 4%, from 1% to 3%, or from 1% to 2%, by weight of the composition.

1.4. Any of the preceding compositions, wherein the acyl glutamate is present in an amount of from 1.5% to 10%, e.g., from 1.5% to 9%, from 1.5% to 8%, from 1.5% to 7%, from 1.5% to 6%, from 1.5% to 5%, from 1.5% to 4%, from 1.5% to 3%, or from 1.5% to 2%, by weight of the composition.

1.5. Any of the preceding compositions, wherein the acyl glutamate is present in an amount of from 2% to 10%, e.g., from 2% to 9%, from 2% to 8%, from 2% to 7%, from 2% to 6%, from 2% to 5%, from 2% to 4%, or from 2% to 3%, by weight of the composition.

1.6. Any of the preceding compositions, wherein the acyl glutamate is present in an amount of from 3% to 10%, e.g., from 3% to 9%, from 3% to 8%, from 3% to 7%, from 3% to 6%, from 3% to 5%, or from 3% to 4%, by weight of the composition.

1.7. Any of the preceding compositions, wherein the acyl glutamate is present in an amount of from 4% to 10%, e.g., from 4% to 9%, from 4% to 8%, from 4% to 7%, from 4% to 6%, or from 4% to 5%, by weight of the composition.

1.8. Any of the preceding compositions, wherein the acyl glutamate is present in an amount of from 5% to 10%, e.g., from 5% to 9%, from 5% to 8%, from 5% to 7%, or from 5% to 6%, by weight of the composition.

1.9. Any of the preceding compositions, wherein the acyl glutamate is present in an amount of from 6% to 10%, e.g., from 6% to 9%, from 6% to 8%, or from 6% to 7%, by weight of the composition.

1.10. Any of the preceding compositions, wherein the acyl glutamate is present in an amount of from 7% to 10%, e.g., from 7% to 9%, or from 7% to 8%, by weight of the composition.

1.11. Any of the preceding compositions, wherein the acyl glutamate is present in an amount of from 8% to 10%, e.g., from 8% to 9% or from 9% to 10%, by weight of the composition.

1.12. Any of the preceding compositions, wherein the acyl glutamate is selected from dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and a combination thereof, preferably sodium cocoyl glutamate, and wherein the acyl glutamate is present in an amount of from 2% to 8% by weight, from 4% to 8% by weight, or from 6% to 8% by weight of the composition.

1.13. Any of the preceding compositions, wherein the composition does not contain any surfactant other than the acyl glutamate.

1.14. Any of the preceding compositions, wherein the composition comprises a co-surfactant.

1.15. Any of the preceding compositions, wherein the co-surfactant comprises an alkyl glucoside.

1.16. Any of the preceding compositions, wherein the alkyl glucoside is present in an amount of from 1% to 9%, e.g., from 2% to 8%, from 2% to 7%, from 2% to 6%, from 2% 5%, from 2% to 4%, from 2% to 3%, from 3% to 8%, from 3% to 7%, from 3% to 6%, from 3% to 5%, from 3% to 4%, from 4% to 8%, from 4% to 7%, from 4% to 6%, from 4% to 5%, from 5% to 8%, from 5% to 7%, from 5% to 6%, from 6% to 8%, from 6% to 7%, or from 7% to 8%, by weight of the composition, optionally wherein the alkyl glucoside is present in an amount of from 2% to 8% by weight, from 2% to 6% by weight, or from 2% to 4% by weight of the composition.

1.17. Any of the preceding compositions, wherein the alkyl glucoside is $C_{8-25}$ alkyl glucoside, e.g., $C_{8-18}$ alkyl glucoside, $C_{10-18}$ alkyl glucoside or $C_{10-16}$ alkyl glucoside, optionally wherein the alkyl glucoside is selected from decyl glucoside, caprylyl/capryl glucoside, lauryl glucoside, coco-glucoside, octyl glucoside, cetearyl glucoside, cetyl glucoside, hexadecyl glucoside, arachidyl glucoside, and a combination thereof.

1.18. Any of the preceding compositions, wherein the alkyl glucoside is selected from decyl glucoside, caprylyl/capryl glucoside and a combination thereof.

1.19. Any of the preceding compositions, wherein the alkyl glucoside is selected from decyl glucoside, caprylyl/capryl glucoside, lauryl glucoside, coco-glucoside, octyl glucoside, cetearyl glucoside, cetyl glucoside, hexadecyl glucoside, arachidyl glucoside, and a combination thereof, preferably selected from decyl glucoside, caprylyl/capryl glucoside and a combination thereof, and the alkyl glucoside is present in an amount of from 2% to 8% by weight, from 2% to 6% by weight, or from 2% to 4% by weight of the composition.

1.20. Any of the preceding compositions, wherein the alkyl glucoside is a combination of decyl glucoside and caprylyl/capryl glucoside, optionally wherein the weight ratio of caprylyl/capryl glucoside to decyl glucoside present in the composition is 2 to 1-4 to 1, preferably about 3 to 1.

1.21. Any of the preceding compositions, wherein the composition does not contain any surfactant other than the acyl glutamate and the alkyl glucoside.

1.22. Any of the preceding compositions, wherein the total amount of surfactants present in the composition is from 8% to 12%, e.g., from 8% to 11%, from 9% to 11%, from 9.5% to 10.5%, or about 10%, by weight of the composition.

1.23. Any of the preceding compositions, wherein the vitamin is selected from vitamin C, vitamin D, vitamin E, vitamin K, and a combination thereof.

1.24. Any of the preceding compositions, wherein the vitamin is vitamin E, optionally wherein the vitamin E is vitamin E acetate or vitamin E succinate, preferably vitamin E acetate.

1.25. Any of the preceding compositions, wherein vitamin E is present in an amount of from 0.05% to 1%, e.g., from 0.05% to 0.5%, from 0.05% to 0.3%, from 0.05% to 0.2%, from 0.05% to 0.15%, or about 0.1%, by weight of the composition.

1.26. Any of the preceding compositions, wherein the composition comprises an oil selected from sunflower seed oil, olive oil, shea butter, jojoba oil, almond oil, grape seed oil, rose hip seed oil, mink oil, castor oil, soybean oil, mineral oil, and a combination thereof, optionally wherein the oil is sunflower seed oil.

1.27. Any of the preceding compositions, wherein the composition comprises a thickener.

1.28. Any of the preceding compositions, wherein the thickener comprises a gum, optionally selected from xanthan gum, carrageenan and a combination thereof.

1.29. Any of the preceding compositions, wherein the composition comprises a humectant, optionally wherein the humectant is selected from glycerin, sorbitol, and a combination thereof.

1.30. Any of the preceding compositions, wherein the composition comprises water.

1.31. Any of the preceding compositions, wherein the composition is free or substantially free of sodium lauryl sulfate (SLS).

1.32. Any of the preceding compositions, wherein the composition is free or substantially free of sodium lauryl ether sulfate (SLES).

1.33. Any of the preceding compositions, wherein the composition is free or substantially free of sodium lauryl sulfate (SLS) and sodium lauryl ether sulfate (SLES).

1.34. Any of the preceding compositions, wherein the composition is free or substantially free of alkyl sulfate salts, e.g., $C_{1-25}$ alkyl sulfate salts.

1.35. Any of the preceding compositions, wherein the composition is free or substantially free of alkyl aryl sulfonate salts, e.g., $C_{1-25}$ alkyl aryl sulfonate salts, e.g., alkyl benzene sulfonate salts, e.g., sodium dodecyl benzene sulfonate.

1.36. Any of the preceding compositions, wherein the composition is free or substantially free of alkyl sulfate salts, e.g., $C_{1-25}$ alkyl sulfate salts, and alkyl aryl sulfonate salts, e.g., $C_{1-25}$ alkyl aryl sulfonate salts.

1.37. Any of the preceding compositions, wherein the composition is free or substantially free of sulfate.

1.38. Any of the preceding compositions, wherein the vitamin is vitamin E, wherein the acyl glutamate is sodium cocoyl glutamate, and optionally wherein the acyl glutamate is present in an amount of from 2% to 8% by weight, from 4% to 8% by weight, or from 6% to 8% by weight of the composition.

1.39. Any of compositions 1.0-1.37, wherein the vitamin is vitamin E, wherein the acyl glutamate is sodium cocoyl glutamate, and wherein the acyl glutamate is present in an amount of from 2% to 12% by weight, e.g., from 2% to 4% by wt. (e.g., about 3.4% by wt.), e.g., from 4% to 8% by weight, e.g., from 6% to 8% by weight of the composition (e.g., about 7.8% by wt.), e.g., from 8%-12% by wt. (e.g., about 10% by wt.).

1.40. Any of the preceding compositions, wherein the vitamin is vitamin E, wherein the acyl glutamate is sodium cocoyl glutamate, wherein the alkyl glucoside is selected from decyl glucoside, caprylyl/capryl glucoside and a combination thereof, wherein the acyl glutamate is present in an amount of from 2% to 8% by weight of the composition and the alkyl glucoside is present in an amount of from 2% to 8% by weight by weight of the composition, and optionally wherein the alkyl glucoside is a combination of decyl glucoside and caprylyl/capryl glucoside.

1.41. Any of the preceding compositions, wherein the vitamin is vitamin E, wherein the acyl glutamate is sodium cocoyl glutamate, wherein the alkyl glucoside is selected from decyl glucoside, caprylyl/capryl glucoside and a combination thereof, wherein the acyl glutamate is present in an amount of from 4% to 8% by weight of the composition and the alkyl glucoside is present in an amount of from 2% to 6% by weight by weight of the composition, and optionally wherein the alkyl glucoside is a combination of decyl glucoside and caprylyl/capryl glucoside.

1.42. Any of the preceding compositions, wherein the vitamin is vitamin E, wherein the acyl glutamate is sodium cocoyl glutamate, wherein the alkyl glucoside is selected from decyl glucoside, caprylyl/capryl glucoside and a combination thereof, wherein the acyl glutamate is present in an amount of from 6% to 8% by weight of the composition and the alkyl glucoside is present in an amount of from 2% to 4% by weight of the composition, and optionally wherein the alkyl glucoside is a combination of decyl glucoside and caprylyl/capryl glucoside.

1.43. Any of the preceding compositions, wherein the composition comprises an acyl glutamate, at least one topically active compound, a humectant, an oil, a surfactant, co-surfactants, and a gum.

1.44. Any of the preceding compositions, wherein the composition further comprises an antiperspirant active, a deodorant active, a gelling agent, an antioxidant, a fragrance, or a combination thereof.

1.45. Any of the preceding compositions, wherein the composition is a rinse off composition, optionally wherein the composition is a liquid soap, liquid hand soap, shower gel, body wash, shampoo, or hair conditioner.

The present disclosure provides, in another aspect, a personal care composition (Composition 2.0), e.g., skin care composition for use in increasing vitamin deposition on the skin of a subject, comprising an acyl glutamate, e.g., sodium cocoyl glutamate, in an amount of from 1% to 10% by weight of the composition and at least one topically active compound, wherein the at least one topically active compound comprises a vitamin.

For example, the composition includes:

2.1. Composition 2.0, wherein the acyl glutamate is $C_{8-25}$ acyl glutamate, e.g., $C_{8-18}$ acyl glutamate, $C_{10-18}$ acyl glutamate, or $C_{10-16}$ acyl glutamate, optionally wherein the acyl glutamate is selected from dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and a combination thereof.

2.2. Any of the preceding compositions, the acyl glutamate is cocoyl glutamate, e.g., sodium cocoyl glutamate.

2.3. Any of the preceding compositions, wherein the acyl glutamate is present in an amount of from 1% to 9%, e.g., from 1% to 8%, from 1% to 7%, from 1% to 6%, from 1% to 5%, from 1% to 4%, from 1% to 3%, or from 1% to 2%, by weight of the composition.

2.4. Any of the preceding compositions, wherein the acyl glutamate is present in an amount of from 1.5% to 10%, e.g., from 1.5% to 9%, from 1.5% to 8%, from 1.5% to 7%, from 1.5% to 6%, from 1.5% to 5%, from 1.5% to 4%, from 1.5% to 3%, or from 1.5% to 2%, by weight of the composition.

2.5. Any of the preceding compositions, wherein the acyl glutamate is present in an amount of from 2% to 10%, e.g., from 2% to 9%, from 2% to 8%, from 2% to 7%, from 2% to 6%, from 2% to 5%, from 2% to 4%, or from 2% to 3%, by weight of the composition.

2.6. Any of the preceding compositions, wherein the acyl glutamate is present in an amount of from 3% to 10%, e.g., from 3% to 9%, from 3% to 8%, from 3% to 7%, from 3% to 6%, from 3% to 5%, or from 3% to 4%, by weight of the composition.

2.7. Any of the preceding compositions, wherein the acyl glutamate is present in an amount of from 4% to 10%, e.g., from 4% to 9%, from 4% to 8%, from 4% to 7%, from 4% to 6%, or from 4% to 5%, by weight of the composition.

2.8. Any of the preceding compositions, wherein the acyl glutamate is present in an amount of from 5% to 10%, e.g., from 5% to 9%, from 5% to 8%, from 5% to 7%, or from 5% to 6%, by weight of the composition.

2.9. Any of the preceding compositions, wherein the acyl glutamate is present in an amount of from 6% to 10%, e.g., from 6% to 9%, from 6% to 8%, or from 6% to 7%, by weight of the composition.

2.10. Any of the preceding compositions, wherein the acyl glutamate is present in an amount of from 7% to 10%, e.g., from 7% to 9%, or from 7% to 8%, by weight of the composition.

2.11. Any of the preceding compositions, wherein the acyl glutamate is present in an amount of from 8% to 10%, e.g., from 8% to 9% or from 9% to 10%, by weight of the composition.

2.12. Any of the preceding compositions, wherein the acyl glutamate is selected from dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and a combination thereof, preferably sodium cocoyl glutamate, and wherein the acyl glutamate is present in an amount of from 2% to 8% by weight, from 4% to 8% by weight, or from 6% to 8% by weight of the composition.

2.13. Any of the preceding compositions, wherein the composition does not contain any surfactant other than the acyl glutamate.

2.14. Any of the preceding compositions, wherein the composition comprises a co-surfactant.

2.15. Any of the preceding compositions, wherein the co-surfactant comprises an alkyl glucoside.

2.16. Any of the preceding compositions, wherein the alkyl glucoside is present in an amount of from 1% to 9%, e.g., from 2% to 8%, from 2% to 7%, from 2% to 6%, from 2% 5%, from 2% to 4%, from 2% to 3%, from 3% to 8%, from 3% to 7%, from 3% to 6%, from 3% to 5%, from 3% to 4%, from 4% to 8%, from 4% to 7%, from 4% to 6%, from 4% to 5%, from 5% to 8%, from 5% to 7%, from 5% to 6%, from 6% to 8%, from 6% to 7%, or from 7% to 8%, by weight of the composition, optionally wherein the alkyl glucoside is present in an amount of from 2% to 8% by weight, from 2% to 6% by weight, or from 2% to 4% by weight of the composition.

2.17. Any of the preceding compositions, wherein the alkyl glucoside is $C_{8-25}$ alkyl glucoside, e.g., $C_{8-18}$ alkyl glucoside, $C_{10-18}$ alkyl glucoside or $C_{10-16}$ alkyl glucoside, optionally wherein the alkyl glucoside is selected from decyl glucoside, caprylyl/capryl glucoside, lauryl glucoside, coco-glucoside, octyl glucoside, cetearyl glucoside, cetyl glucoside, hexadecyl glucoside, arachidyl glucoside, and a combination thereof.

2.18. Any of the preceding compositions, wherein the alkyl glucoside is selected from decyl glucoside, caprylyl/capryl glucoside and a combination thereof.

2.19. Any of the preceding compositions, wherein the alkyl glucoside is selected from decyl glucoside, caprylyl/capryl glucoside, lauryl glucoside, coco-glucoside, octyl glucoside, cetearyl glucoside, cetyl glucoside, hexadecyl glucoside, arachidyl glucoside, and a combination thereof, preferably selected from decyl glucoside, caprylyl/capryl glucoside and a combination thereof, and the alkyl glucoside is present in an amount of from 2% to 8% by weight, from 2% to 6% by weight, or from 2% to 4% by weight of the composition.

2.20. Any of the preceding compositions, wherein the alkyl glucoside is a combination of decyl glucoside and caprylyl/capryl glucoside, optionally wherein the weight ratio of caprylyl/capryl glucoside to decyl glucoside present in the composition is 2 to 1-4 to 1, e.g., about 3 to 1.

2.21. Any of Compositions 2.14 to 2.20, wherein the composition does not contain any surfactant other than the acyl glutamate and the alkyl glucoside.

2.22. Any of the preceding compositions, wherein the total amount of surfactants present in the composition is from 8% to 12%, e.g., from 8% to 11%, from 9% to 11%, from 9.5% to 10.5%, or about 10%, by weight of the composition, from 9% to 11% by weight of the composition.

2.23. Any of the preceding compositions, wherein the vitamin is selected from vitamin C, vitamin D, vitamin E, vitamin K, and a combination thereof.

2.24. Any of the preceding compositions, wherein the vitamin is vitamin E, optionally wherein the vitamin E is vitamin E acetate or vitamin E succinate, preferably vitamin E acetate.

2.25. Any of the preceding compositions, wherein vitamin E is present in an amount of from 0.05% to 1%, e.g., from 0.05% to 0.5%, from 0.05% to 0.3%, from 0.05% to 0.2%, from 0.05% to 0.15%, or about 0.1%, by weight of the composition.

2.26. Any of the preceding compositions, wherein the composition comprises an oil selected from sunflower seed oil, olive oil, shea butter, jojoba oil, almond oil, grape seed oil, rose hip seed oil, mink oil, castor oil, soybean oil, mineral oil, and a combination thereof, optionally wherein the oil is sunflower seed oil.

2.27. Any of the preceding compositions, wherein the composition comprises a thickener.

2.28. Any of the preceding compositions, wherein the thickener comprises a gum, optionally selected from xanthan gum, carrageenan and a combination thereof.

2.29. Any of the preceding compositions, wherein the composition comprises a humectant, optionally wherein the humectant is selected from glycerin, sorbitol, and a mixture thereof.

2.30. Any of the preceding compositions, wherein the composition comprises water, 2.31. Any of the preceding compositions, wherein the composition is free or substantially free of sodium lauryl sulfate (SLS).

2.32. Any of the preceding compositions, wherein the composition is free or substantially free of sodium lauryl ether sulfate (SLES).

2.33. Any of the preceding compositions, wherein the composition is free or substantially free of sodium lauryl sulfate (SLS) and sodium lauryl ether sulfate (SLES).

2.34. Any of the preceding compositions, wherein the composition is free or substantially free of alkyl sulfate salts, e.g., $C_{1-25}$ alkyl sulfate salts.

2.35. Any of the preceding compositions, wherein the composition is free or substantially free of alkyl aryl sulfonate salts, e.g., $C_{1-25}$ alkyl aryl sulfonate salts, e.g., alkyl benzene sulfonate salts, e.g., sodium dodecyl benzene sulfonate.

2.36. Any of the preceding compositions, wherein the composition is free or substantially free of alkyl sulfate salts, e.g., $C_{1-25}$ alkyl sulfate salts, and alkyl aryl sulfonate salts, e.g., $C_{1-25}$ alkyl aryl sulfonate salts.

2.37. Any of the preceding compositions, wherein the composition is free or substantially free of sulfate.

2.38. Any of the preceding compositions, wherein the vitamin is vitamin E, wherein the acyl glutamate is sodium cocoyl glutamate, and optionally wherein the acyl glutamate is present in an amount of from 2% to 8% by weight, from 4% to 8% by weight, or from 6% to 8% by weight of the composition.

2.39. Any of the preceding compositions, wherein the vitamin is vitamin E, wherein the acyl glutamate is sodium cocoyl glutamate, wherein the alkyl glucoside is selected from decyl glucoside, caprylyl/capryl glucoside and a combination thereof, wherein the acyl glutamate is present in an amount of from 2% to 8% by weight of the composition and the alkyl glucoside is present in an amount of from 2% to 8% by weight by weight of the composition, and optionally wherein the alkyl glucoside is a combination of decyl glucoside and caprylyl/capryl glucoside.

2.40. Any of the preceding compositions, wherein the vitamin is vitamin E, wherein the acyl glutamate is sodium cocoyl glutamate, wherein the alkyl glucoside is selected from decyl glucoside, caprylyl/capryl glucoside and a combination thereof, wherein the acyl glutamate is present in an amount of from 4% to 8% by weight of the composition and the alkyl glucoside is present in an amount of from 2% to 6% by weight by weight of the composition, and optionally wherein the alkyl glucoside is a combination of decyl glucoside and caprylyl/capryl glucoside.

2.41. Any of the preceding compositions, wherein the vitamin is vitamin E, wherein the acyl glutamate is sodium cocoyl glutamate, wherein the alkyl glucoside is selected from decyl glucoside, caprylyl/capryl glucoside and a combination thereof, wherein the acyl glutamate is present in an amount of from 6% to 8% by weight of the composition and the alkyl glucoside is present in an amount of from 2% to 4% by weight of the composition, and optionally wherein the alkyl glucoside is a combination of decyl glucoside and caprylyl/capryl glucoside.

2.42. Any of the preceding compositions, wherein the vitamin is vitamin E and wherein the acyl glutamate is sodium cocoyl glutamate, optionally wherein the vitamin E deposition on the skin of the subject is from 0.3 µg/cm² to 1.75 µg/cm², e.g., from 0.4 µg/cm² to 1.75 µg/cm², or from 0.45 µg/cm² to 1.75 µg/cm².

2.43. Any of the preceding compositions, wherein the vitamin is vitamin E, wherein the acyl glutamate is sodium cocoyl glutamate, and wherein the alkyl glucoside is caprylyl/capryl glucoside, optionally wherein the vitamin E deposition on the skin of the subject is from 0.3 µg/cm² to 1.75 µg/cm², e.g., from 0.4 µg/cm² to 1.75 µg/cm², or from 0.45 µg/cm² to 1.75 µg/cm².

2.44. Any of the preceding compositions, wherein the composition comprises an acyl glutamate, at least one topically active compound, a humectant, an oil, a surfactant, co-surfactants, and a gum.

2.45. Any of the preceding compositions, wherein the composition further comprises an antiperspirant active, a deodorant active, a gelling agent, an antioxidant, a fragrance, or a combination thereof.

2.46. Any of the preceding compositions, wherein the composition is a rinse off composition, optionally wherein the composition is a liquid soap, liquid hand soap, shower gel, body wash, shampoo, or hair conditioner.

In some embodiments, the acyl glutamate is $C_{8-25}$ acyl glutamate, e.g., $C_{8-18}$ acyl glutamate, $C_{10-18}$ acyl glutamate, or $C_{10-16}$ acyl glutamate, optionally wherein the acyl glutamate is selected from dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and a combination thereof, preferably sodium cocoyl glutamate. In some embodiments, the acyl glutamate is cocoyl glutamate, e.g., sodium cocoyl glutamate.

In some embodiments, the acyl glutamate is present in an amount of from 1% to 9%, e.g., from 1% to 8%, from 1% to 7%, from 1% to 6%, from 1% to 5%, from 1% to 4%, from 1% to 3%, or from 1% to 2%, by weight of the composition.

In some embodiments, the acyl glutamate is present in an amount of from 1.5% to 10%, e.g., from 1.5% to 9%, from 1.5% to 8%, from 1.5% to 7%, from 1.5% to 6%, from 1.5% to 5%, from 1.5% to 4%, from 1.5% to 3%, or from 1.5% to 2%, by weight of the composition.

In some embodiments, the acyl glutamate is present in an amount of from 2% to 10%, e.g., from 2% to 9%, from 2% to 8%, from 2% to 7%, from 2% to 6%, from 2% to 5%, from 2% to 4%, or from 2% to 3%, by weight of the composition.

In some embodiments, the acyl glutamate is present in an amount of from 3% to 10%, e.g., from 3% to 9%, from 3% to 8%, from 3% to 7%, from 3% to 6%, from 3% to 5%, or from 3% to 4%, by weight of the composition.

In some embodiments, the acyl glutamate is present in an amount of from 4% to 10%, e.g., from 4% to 9%, from 4% to 8%, from 4% to 7%, from 4% to 6%, or from 4% to 5%, by weight of the composition.

In some embodiments, the acyl glutamate is present in an amount of from 5% to 10%, e.g., from 5% to 9%, from 5% to 8%, from 5% to 7%, or from 5% to 6%, by weight of the composition.

In some embodiments, the acyl glutamate is present in an amount of from 6% to 10%, e.g., from 6% to 9%, from 6% to 8%, or from 6% to 7%, by weight of the composition.

In some embodiments, the acyl glutamate is present in an amount of from 7% to 10%, e.g., from 7% to 9%, or from 7% to 8%, by weight of the composition.

In some embodiments, the acyl glutamate is present in an amount of from 8% to 10%, e.g., from 8% to 9% or from 9% to 10%, by weight of the composition.

In some embodiments, the acyl glutamate is selected from dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and a combination thereof, preferably sodium cocoyl glutamate, and the acyl glutamate is present in an amount of from 2% to 8% by weight, from 4% to 8% by weight, or from 6% to 8% by weight of the composition.

In some embodiments, the composition does not contain any surfactant other than the acyl glutamate.

In some embodiments, the composition comprises a co-surfactant. In some embodiments, the co-surfactant comprises an alkyl glucoside.

In some embodiments, the alkyl glucoside is present in an amount of from 1% to 9%, e.g., from 2% to 8%, from 2% to 7%, from 2% to 6%, from 2% 5%, from 2% to 4%, from 2% to 3%, from 3% to 8%, from 3% to 7%, from 3% to 6%, from 3% to 5%, from 3% to 4%, from 4% to 8%, from 4% to 7%, from 4% to 6%, from 4% to 5%, from 5% to 8%, from 5% to 7%, from 5% to 6%, from 6% to 8%, from 6% to 7%, or from 7% to 8%, by weight of the composition. In some embodiments, the alkyl glucoside is present in an amount of from 2% to 8% by weight, from 2% to 6% by weight, or from 2% to 4% by weight of the composition.

In some embodiment, the alkyl glucoside is $C_{8-25}$ alkyl glucoside, e.g., $C_{8-18}$ alkyl glucoside, $C_{10-18}$ alkyl glucoside or $C_{10-16}$ alkyl glucoside, optionally wherein the alkyl glucoside is selected from decyl glucoside, caprylyl/capryl glucoside, lauryl glucoside, coco-glucoside, octyl glucoside, cetearyl glucoside, cetyl glucoside, hexadecyl glucoside, arachidyl glucoside, and a combination thereof.

In some embodiments, the alkyl glucoside is selected from decyl glucoside, caprylyl/capryl glucoside and a combination thereof.

In some embodiments, the alkyl glucoside is selected from decyl glucoside, caprylyl/capryl glucoside, lauryl glucoside, coco-glucoside, octyl glucoside, cetearyl glucoside, cetyl glucoside, hexadecyl glucoside, arachidyl glucoside, and a combination thereof, preferably selected from decyl glucoside, caprylyl/capryl glucoside and a combination thereof, and the alkyl glucoside is present in an amount of from 2% to 8% by weight, from 2% to 6% by weight, or from 2% to 4% by weight of the composition.

In some embodiments, the alkyl glucoside is a combination of decyl glucoside and caprylyl/capryl glucoside, optionally wherein the weight ratio of caprylyl/capryl glucoside to decyl glucoside present in the composition is 2 to 1 or 4 to 1, preferably about 3 to 1.

In some embodiments, the composition does not contain any surfactant other than the acyl glutamate and the alkyl glucoside.

In some embodiments, the total amount of surfactants present in the composition is from 0.1% to 20% by wt. of the total composition. In some embodiments, the total amount of surfactants present in the composition is from 8% to 12%, e.g., from 8% to 11%, from 9% to 11%, from 9.5% to 10.5%, or about 10%, by weight of the total composition.

In some embodiments, the vitamin is selected from vitamin C, vitamin D, vitamin E, vitamin K, and a combination thereof.

In some embodiments, the vitamin is vitamin E, optionally wherein the vitamin E is vitamin E acetate or vitamin E succinate, preferably vitamin E acetate.

In some embodiments, vitamin E is present in an amount of from 0.05% to 1%, e.g., from 0.05% to 0.5%, from 0.05% to 0.3%, from 0.05% to 0.2%, from 0.05% to 0.15%, or about 0.1%, by weight of the composition.

Many personal care products incorporate oil such as sunflower seed oil, which provides more "crème like" appearance and/or other benefits. The addition of sunflower seed oil causes the initial formulation to go from a roughly homogenous mixture to an oil in water emulsion. In some embodiments, the composition comprises an oil selected from sunflower seed oil, olive oil, shea butter, jojoba oil, almond oil, grape seed oil, rose hip seed oil, mink oil, castor oil, soybean oil, mineral oil, and a combination thereof, optionally wherein the oil is sunflower seed oil.

In some embodiments, the composition comprises a thickener. In some embodiments, the thickener comprises a gum, optionally selected from xanthan gum, carrageenan and a combination thereof.

In some embodiments, the composition comprises a humectant, optionally wherein the humectant is selected from glycerin, sorbitol, and a combination thereof.

In some embodiments, the composition comprises water.

In some embodiments, wherein the composition is free or substantially free of sodium lauryl sulfate (SLS). In some embodiments, the composition is free or substantially free of sodium lauryl ether sulfate (SLES). In some embodiments, the composition is free or substantially free of sodium lauryl sulfate (SLS) and sodium lauryl ether sulfate (SLES). In some embodiments, the composition is free or substantially free of alkyl sulfate salts, e.g., $C_{1-25}$ alkyl sulfate salts. In some embodiments, the composition is free or substantially free of alkyl aryl sulfonate salts, e.g., $C_{1-25}$ alkyl aryl sulfonate salts, e.g., alkyl benzene sulfonate salts, e.g., sodium dodecyl benzene sulfonate. In some embodiments, the composition is free or substantially free of alkyl sulfate salts, e.g., $C_{1-25}$ alkyl sulfate salts, and alkyl aryl sulfonate salts, e.g., $C_{1-25}$ alkyl aryl sulfonate salts.

In some embodiments, the composition is free or substantially free of sulfate.

In some embodiments, the vitamin is vitamin E and the acyl glutamate is sodium cocoyl glutamate, optionally wherein the acyl glutamate is present in an amount of from 2% to 8% by weight, from 4% to 8% by weight, or from 6% to 8% by weight of the composition.

In some embodiments, the vitamin is vitamin E, the acyl glutamate is sodium cocoyl glutamate, the alkyl glucoside is selected from decyl glucoside, caprylyl/capryl glucoside and a combination thereof, the acyl glutamate is present in an amount of from 2% to 8% by weight of the composition, and the alkyl glucoside is present in an amount of from 2% to 8% by weight by weight of the composition, optionally wherein the alkyl glucoside is a combination of decyl glucoside and caprylyl/capryl glucoside.

In some embodiments, the vitamin is vitamin E, the acyl glutamate is sodium cocoyl glutamate, the alkyl glucoside is selected from decyl glucoside, caprylyl/capryl glucoside and a combination thereof, the acyl glutamate is present in an amount of from 4% to 8% by weight of the composition, and the alkyl glucoside is present in an amount of from 2% to 6% by weight by weight of the composition, optionally wherein the alkyl glucoside is a combination of decyl glucoside and caprylyl/capryl glucoside.

In some embodiments, the vitamin is vitamin E, the acyl glutamate is sodium cocoyl glutamate, the alkyl glucoside is selected from decyl glucoside, caprylyl/capryl glucoside and a combination thereof, the acyl glutamate is present in an amount of from 6% to 8% by weight of the composition, and the alkyl glucoside is present in an amount of from 2% to 4% by weight of the composition, optionally wherein the alkyl glucoside is a combination of decyl glucoside and caprylyl/capryl glucoside.

In some embodiments, the composition comprises an acyl glutamate, at least one topically active compound, a humectant, an oil, a surfactant, co-surfactants, and a gum.

In some embodiments, the composition further comprises an antiperspirant active, a deodorant active, a gelling agent, an antioxidant, a fragrance, or a combination thereof.

In some embodiments, the composition is a rinse off composition, optionally wherein the composition is a liquid soap, liquid hand soap, shower gel, body wash, shampoo, or hair conditioner.

In some embodiments, e.g., any of Compositions 1 et seq. or Composition 2 et seq., the vitamin is vitamin E and the acyl glutamate is sodium cocoyl glutamate, optionally wherein the vitamin E deposition on the skin of the subject is from 0.3 µg/cm$^2$ to 1.75 µg/cm$^2$, e.g., from 0.4 µg/cm$^2$ to 1.75 µg/cm$^2$, or from 0.45 µg/cm$^2$ to 1.75 µg/cm$^2$.

In some embodiments, e.g., any of Compositions 1 et seq. or Composition 2 et seq., the vitamin is vitamin E acetate, the acyl glutamate is sodium cocoyl glutamate, and the alkyl glucoside is caprylyl/capryl glucoside, optionally wherein the vitamin E acetate deposition on the skin of the subject is from 0.3 µg/cm$^2$ to 1.75 µg/cm$^2$, e.g., from 0.4 µg/cm$^2$ to 1.75 µg/cm$^2$, or from 0.45 µg/cm$^2$ to 1.75 µg/cm$^2$.

The composition of the present disclosure may be any type of personal care composition. In certain embodiments, the composition is any composition that can be formulated into topical skin care formulations suitable for application to skin. Examples of such compositions include, but are not limited to, personal care compositions, skin care compositions, antiperspirants, deodorants, body washes, creams, shower gels, bar soaps, shampoo, hair conditioners, and cosmetics. In some embodiments, the composition is a rinse off product (liquid soap, liquid hand soap, shower gel, body wash, shampoo, or hair conditioner, etc.). The composition can comprise a single phase or can be a multi-phase system, for example a system comprising a polar phase and an oil phase, optionally in the form of a stable emulsion. The composition can be liquid, semi-solid or solid. The formulation can be provided in any suitable container such as an aerosol can, tube or container with a porous cap, roll-on container, bottle, container with an open end, etc.

Water may be present in the composition. Water employed in the preparation of commercial personal care compositions should be deionized and free of organic impurities. Water commonly makes up the balance of the compositions and includes about 10% to about 90%, or about 10% to about 80%, by weight of the personal care compositions. This amount of water includes the free water which is added plus that amount which is introduced with other materials such as glycerin, sorbitol or any components of the disclosure.

In some embodiments the disclosure provides a sulfate-free personal care formulation comprising a surfactant system, humectants, antioxidants, pH adjusters, vitamins, fragrances, thickeners, oils, and water.

The pH adjusters of the present disclosure comprise but are not limited to lactic acid, sodium hydroxide, citric acid.

In some embodiments the disclosure provides a sulfate-free personal care formulation comprising an antibacterial agent. The antibacterial agent of the disclosure may be lactic acid.

The surfactant system of the present disclosure comprises an acyl glutamate in an amount of from 1% to 10% by weight of the composition. Acyl glutamate is a compound in which an acyl group is linked to glutamate by an amide bond. Acyl refers to a moiety containing a double-bonded oxygen group and an alkyl group (R—C=O). As used herein, the term "acyl glutamate" may be or include free form or any acceptable salts thereof. The salt may be sodium or potassium. For example, the structure of sodium cocoyl glutamate is shown below:

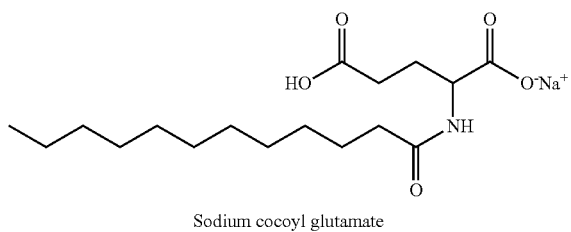

Sodium cocoyl glutamate

Acyl glutamates which can be used in the composition may be $C_{8-25}$ acyl glutamate, e.g., $C_{8-18}$ acyl glutamate, $C_{10-18}$ acyl glutamate, or $C_{10-16}$ acyl glutamate. The acyl group may be branched or unbranched. In some embodiments, the acyl group is unbranched. The acyl group may be saturated or unsaturated. In some embodiments, the acyl group is saturated. In some embodiments, the acyl glutamate is selected from dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and a combination thereof. In some embodiments, the acyl glutamate is cocoyl glutamate, e.g., sodium cocoyl glutamate. In some embodiments, the composition does not contain any surfactant other than the acyl glutamate.

In some embodiments, the acyl glutamate is present in an amount of from 1% to 9%, e.g., from 1% to 8%, from 1% to 7%, from 1% to 6%, from 1% to 5%, from 1% to 4%, from 1% to 3%, or from 1% to 2%, by weight of the composition. In some embodiments, the acyl glutamate is present in an amount of from 1.5% to 10%, e.g., from 1.5% to 9%, from 1.5% to 8%, from 1.5% to 7%, from 1.5% to 6%, from 1.5% to 5%, from 1.5% to 4%, from 1.5% to 3%, or from 1.5% to 2%, by weight of the composition. In some embodiments, the acyl glutamate is present in an amount of from 2% to 10%, e.g., from 2% to 9%, from 2% to 8%, from 2% to 7%, from 2% to 6%, from 2% to 5%, from 2% to 4%, or from 2% to 3%, by weight of the composition. In some embodiments, the acyl glutamate is present in an amount of from 3% to 10%, e.g., from 3% to 9%, from 3% to 8%, from 3% to 7%, from 3% to 6%, from 3% to 5%, or from 3% to 4%, by weight of the composition. In some embodiments, the acyl glutamate is present in an amount of from 4% to 10%, e.g., from 4% to 9%, from 4% to 8%, from 4% to 7%, from 4% to 6%, or from 4% to 5%, by weight of the composition. In some embodiments, the acyl glutamate is present in an amount of from 5% to 10%, e.g., from 5% to 9%, from 5% to 8%, from 5% to 7%, or from 5% to 6%, by weight of the composition. In some embodiments, the acyl glutamate is present in an amount of from 6% to 10%, e.g., from 6% to 9%, from 6% to 8%, or from 6% to 7%, by weight of the composition. In some embodiments, the acyl glutamate is present in an amount of from 7% to 10%, e.g., from 7% to 9%, or from 7% to 8%, by weight of the composition. In some embodiments, the acyl glutamate is present in an amount of from 8% to 10%, e.g., from 8% to 9% or from 9% to 10%, by weight of the composition.

In some embodiments, the composition does not contain any surfactant other than the acyl glutamate.

In some embodiments, the surfactant system of the present disclosure may comprise a co-surfactant. Additional surfactants, which may be zwitterionic or nonionic, and are known for use in personal care compositions, may be used as a co-surfactant. In some embodiments, the co-surfactant may comprise an alkyl glucoside. Alkyl glucoside is a compound produced by combining a sugar such as glucose with a fatty alcohol. Alkyl refers to unbranched or branched carbon chain. In some embodiments, the alkyl group is unbranched. The alkyl group may be saturated or unsaturated. In some embodiments, the alkyl group is saturated. For example, the structure of decyl glucoside is shown below:

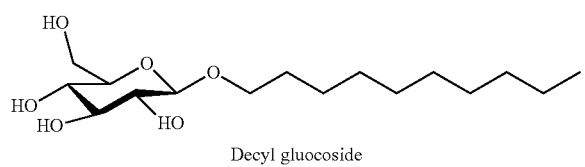

Decyl gluocoside

Alkyl glucoside may be $C_{8-25}$ alkyl glucoside, e.g., $C_{8-18}$ alkyl glucoside, $C_{10-18}$ alkyl glucoside or $C_{10-16}$ alkyl glucoside. In some embodiments, the alkyl glucoside is selected from decyl glucoside, caprylyl/capryl glucoside, lauryl glucoside, coco-glucoside, octyl glucoside, cetearyl glucoside, cetyl glucoside, hexadecyl glucoside, arachidyl glucoside, and a combination thereof. In some embodiments, the alkyl glucoside is selected from decyl glucoside, caprylyl/capryl glucoside and a combination thereof. In some embodiments, the weight ratio of caprylyl/capryl glucoside to decyl glucoside present in the composition is 2 to 1 or 4 to 1, e.g., about 3 to 1. In some embodiments, the alkyl glucoside is present in an amount of from 1% to 9%, e.g., from 2% to 8%, from 2% to 7%, from 2% to 6%, from 2% 5%, from 2% to 4%, from 2% to 3%, from 3% to 8%, from 3% to 7%, from 3% to 6%, from 3% to 5%, from 3% to 4%, from 4% to 8%, from 4% to 7%, from 4% to 6%, from 4% to 5%, from 5% to 8%, from 5% to 7%, from 5% to 6%, from 6% to 8%, from 6% to 7%, or from 7% to 8%, by weight of the composition.

In some embodiments, the acyl glutamate is present in an amount of from 2% to 8% by weight of the composition and the alkyl glucoside is present in an amount of from 2% to 8% by weight by weight of the composition. In some embodiments, the acyl glutamate is present in an amount of from 4% to 8% by weight of the composition and the alkyl glucoside is present in an amount of from 2% to 6% by weight by weight of the composition. In some embodiments, the acyl glutamate is present in an amount of from 6% to 8% by weight of the composition and the alkyl glucoside is present in an amount of from 2% to 4% by weight of the composition.

In some embodiments, the composition does not contain any surfactant other than the acyl glutamate and the alkyl glucoside.

In some embodiments, the co-surfactant may comprise a betaine zwitterionic surfactant, optionally together with an alkyl glucoside. The betaine zwitterionic surfactant may be a $C_8$-$C_{16}$ aminopropyl betaine, e.g., cocamidopropyl betaine. In some embodiments, the co-surfactant may comprise a non-ionic block copolymer, optionally together with an alkyl glucoside. The non-ionic block copolymer may be a poly(propylene oxide)/poly(ethylene oxide) copolymer. In some embodiments, the copolymer has a polyoxypropylene molecular mass of from 3000 to 5000 g/mol and a polyoxyethylene content of from 60 to 80 mol %. In some embodiments, the non-ionic block copolymer is a poloxamer. In some embodiments, the non-ionic block copolymer is selected from: Poloxamer 338, Poloxamer 407, Poloxamer, 237, Poloxamer, 217, Poloxamer 124, Poloxamer 184, Poloxamer 185, and a combination of two or more thereof. In some embodiments, the copolymer is Poloxamer 407. In some embodiments, the co-surfactant may comprise a betaine zwitterionic surfactant and a non-ionic block copolymer, optionally together with an alkyl glucoside.

In some embodiments, the personal care composition may be free or substantially free of sodium lauryl sulfate (SLS) and/or sodium lauryl ether sulfate (SLES). In some embodiments, the composition may be free or substantially free of alkyl sulfate salts. In some embodiment, the alkyl sulfate salts are $C_{1-25}$ alkyl sulfate which may be saturated or unsaturated, and unbranched or branched. In some embodiments, the personal care composition may be free or substantially free of alkyl aryl sulfonate salts, e.g., alkyl benzene sulfonate salts, e.g., sodium dodecyl benzene sulfonate. In some embodiments, the personal care composition may be free or substantially free of alkyl sulfate salts and alkyl aryl sulfonate salts. In some embodiments, the composition may be free or substantially free of sulfate. As used herein, "substantially free" of a material may refer to a composition where the material is present in an amount of less than 0.1 weight %, less than 0.05 weight %, less than 0.01 weight %, less than 0.005 weight %, less than 0.001 weight %, or less than 0.0001 weight % based on a total weight of the composition.

In some embodiments, the total amount of surfactants present in the personal care composition may be from 8% to 12%, e.g., from 8% to 11%, from 9% to 11%, from 9.5% to 10.5% or about 10%, preferably from 9% to 11% by weight of the composition.

The surfactant system disclosed in this disclosure increases the deposition of topically active compounds on the skin when the surfactant system is used in personal care compositions, e.g., skin care compositions. Topically active compounds encompass a wide range of materials, including antibacterial agents, vitamins, medicaments, fragrance materials, antioxidants, antiperspirant actives, deodorant actives, and other skin-care ingredients. The personal care composition of the present disclosure comprises a vitamin. Illustrative vitamins may be or include, but are not limited to, vitamin C, vitamin D, vitamin E, vitamin K, and a combination thereof. In some embodiments, the composition comprises vitamin E, e.g., vitamin E acetate. In some embodiments, Vitamin E may be present in an amount of from 0.05% to 1%, e.g., from 0.05% to 0.5%, from 0.05% to 0.3%, from 0.05% to 0.2%, from 0.05% to 0.15%, or about 0.1%, by weight of the composition.

Vitamin E is a family of four isomers of tocopherols and four isomers of tocotrienols. All eight isomers of vitamin E have a 6-chromanol ring structure and a side chain. The four tocopherols include fully saturated side chains and include alpha-tocopherol, gamma-tocopherol, beta-tocopherol, and delta-tocopherol. The four tocotrienols include unsaturated side chains and include alpha-tocotrienol, gamma-tocotrienol, beta-tocotrienol, and delta-tocotrienol. As used herein, the term "vitamin E" may refer to any one or more of the eight isomers. For example, as used herein, vitamin E may be or include one or more of alpha-tocopherol, gamma-tocopherol, beta-tocopherol, delta-tocopherol, alpha-tocotrienol, gamma-tocotrienol, beta-tocotrienol, delta-tocotrienol, or any combination thereof. In at least one implementation, the vitamin E includes at least one of the four tocopherols. In a preferred implementation, the vitamin E includes gamma-tocopherol, and gamma-tocopherol may make up the major component of the vitamin E. For example, the vitamin E may include gamma-tocopherol in an amount relatively greater than any one or more of the other isomers of vitamin E. In at least one implementation, the vitamin E includes only gamma-tocopherol or includes substantially only gamma-tocopherol. It should be appreciated that the vitamin E and/or the isomers thereof may be or include natural forms of vitamin E, synthetic forms of vitamin E, or combinations thereof. Any one or more of the isomers of vitamin E may be in the "d" form, the "l" form, or combinations thereof. In some embodiments, vitamin E is vitamin E acetate or Vitamin E succinate. In some embodiments, vitamin E is vitamin E acetate.

Vitamin C may be ascorbic acid or derivatives thereof. Ascorbic acid exists as two enantiomers commonly denoted "l" (for "levo") and "d" (for "dextro"). The "l" isomer is the one most often encountered. Ascorbic acid is also referred to as L(+)-ascorbic acid or l-ascorbic acid. The ascorbic acid derivatives may be or include, but are not limited to, L-ascorbic acid, calcium ascorbate, calcium l-ascorbate dihydrate, magnesium ascorbate, potassium ascorbate, magnesium L-ascorbyl phosphate (also referred to as: magnesium ascorbate phosphate or ascorbic acid phosphate magnesium salt), L-ascorbic acid 2-phosphate sesquimagnesium salt hydrate, (+) sodium L-ascorbate, dehydro-l-(+)-ascorbic acid dimer, sodium ascorbyl phosphate (also referred to as: ascorbic acid phosphate sodium salt, sodium l-ascorbyl phosphate, 2-phospho-L-ascorbic acid trisodium salt, L-ascorbic acid 2-phosphate trisodium salt or sodium L-ascorbyl-2-phosphate), ascorbic acid-2-glucoside, ascorbyl dipalmitate, ascorbyl methylsilanol pectinate, ascorbyl stearate, disodium ascorbyl sulfate, ascorbyl 6-palmitate, calcium ascorbyl phosphate, ascorbyl acetate, ascorbyl propionate, ascorbyl stearate, ascorbyl palmitate, ascorbyl dipalmitate, ascorbyl glucoside, ascorbic acid polypeptide, ethyl ascorbyl ether, ascorbyl ethyl silanol pectinate, or the like, or combinations thereof.

Vitamin D is a group of fat-soluble secosteroids responsible for increasing intestinal absorption of calcium, magnesium, and phosphate, and many other biological effects. The two major forms are vitamin $D_2$ or ergocalciferol, and vitamin $D_3$ or cholecalciferol. Vitamin D includes vitamin $D_1$ (mixture of molecular compounds of ergocalciferol with lumisterol), vitamin $D_2$ (ergocalciferol), vitamin $D_3$ (cholecalciferol), vitamin $D_4$ (22-dihydroergocalciferol), and vitamin $D_5$ (sitocalciferol).

Vitamin K is a group of compounds with a common chemical structure of 2-methyl-1,4-naphthoquinone. Vitamin K plays a role in blood clotting, bone metabolism, and regulating blood calcium levels. Vitamin K includes vitamin $K_1$ (phylloquinone) and vitamin $K_2$ (menaquinone). Vitamin $K_2$ have unsaturated isoprenyl side chains and are designated as MK-4 through MK-13, based on the length of their side chain.

Optional ingredients that may be included in the personal care composition of the disclosure include solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments.

The composition may optionally contain emollients in any desired amount to achieve a desired emollient effect. Emollients are known in the art and are used to impart a soothing effect on the skin. Non-volatile emollients are preferable. Classes of non-volatile emollients include non-silicone and silicone emollients. Non-volatile, non-silicone emollients include $C_{12-15}$ alkyl benzoate. The non-volatile silicone material can be a polyethersiloxane, polyalkyaryl-siloxane or polyethersiloxane copolymer. An illustrative non-volatile silicone material is phenyl trimethicone. Examples include, but are not limited to, PPG-14 butyl ether, PPG-3 myristyl ether, secondary alcohol ethoxylates, stearyl alcohol, stearic acid and salts thereof, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl)adipate), Di-(2-ethyl hexyl)succinate, isopropyl myristate, isopropyl palmitate, isopropyl stearate, octacosanol, butyl stearate, glyceryl monostearate, polyethylene glycols, oleic acid, triethylene glycol, lanolin, castor oil, sunflower seed oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide. In some embodiments, the composition comprises an oil selected from sunflower seed oil, olive oil, shea butter, jojoba oil, almond oil, grape seed oil, rose hip seed oil, mink oil, castor oil, soybean oil, mineral oil, and a combination thereof. In certain embodiment, the composition comprises sunflower seed oil.

The composition may include one or more humectants. Humectants can reduce evaporation and also contribute towards preservation by lowering water activity and can also impart desirable sweetness or flavor to compositions. Illustrative humectants may be or include, but are not limited to, glycerin, propylene glycol, polyethylene glycol, sorbitol, xylitol, or the like, or any mixture or combination thereof. In some embodiments, the humectant is selected from glycerin, sorbitol and a combination thereof. In certain embodiments the humectant is glycerin.

The compositions disclosed herein may include thickeners. Illustrative thickeners may be or include, but are not limited to, colloidal silica, fumed silica, a cross-linked polyvinylpyrrolidone (PVP) polymer, cross-linked polyvinylpyrrolidone (PVP), or the like, or mixtures or combinations thereof. In some embodiments, the thickening system includes a cross-linked polyvinylpyrrolidone (PVP) polymer. Illustrative thickeners may also be or include, but are not limited to, carbomers (e.g., carboxyvinyl polymers), carrageenans (e.g., Irish moss, carrageenan, iota-carrageenan, etc.), high molecular weight polyethylene glycols, cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, or the like, or mixtures or combinations thereof. In some embodiments, the thickener comprises or is a gum, optionally selected from xanthan gum, carrageenan, and a combination thereof.

The personal care composition may comprise antiperspirant actives. The additional active antiperspirant ingredient may be selected from aluminum salts, zirconium salts and zinc salts. In some embodiment, the personal care composition may comprise an aluminum containing antiperspirant active. Any of the known aluminum containing antiperspirant active materials can be utilized in the composition. Aluminum containing antiperspirant actives include, but are not limited to, aluminum chlorohydrate, aluminum chloride, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum, sesquichlorohydrate polyethylene glycol, aluminum sesquichlorohydrate propylene glycol.

The personal care composition may include any known deodorant active. Examples of deodorant actives include, but are not limited to, antimicrobial actives, alcohols, 2,4,4'-trichloro-2'-hydroxy diphenyl ether (Triclosan), benzethonium chloride, polyhexamethylene biguanides, triethyl-citrate, 2-amino-2-methyl-1-propanol (AMP), cetyl-trimethylammomium bromide, cetyl pyridinium chloride, farnesol (3,7, 11-trimethyl-2,6,10-dodecatrien-1-ol), N-(4-chlorophenyl)-N'-(3,4-dichlorophenyl)urea (Triclocarban), silver halides, octoxyglycerin (Sensiva™ SC 50) and various zinc salts (for example, zinc ricinoleate), bactericides, and/or bacteriostats. The deodorant active can be included in the composition in an amount of 0-5%, or 0.01-1% by weight, of the total weight of the composition. Triclosan can be included in an amount of 0.05% to 0.5% by weight, of the total weight of the composition.

Gelling agents may be included in the personal care composition. Examples of gelling agents include, but are not limited to, waxes, esters of fatty acid and fatty alcohol, triglycerides, partially or fully hydrogenated soybean oil, partially or fully hydrogenated castor oil, other partial or fully hydrogenated plant oils, stearyl alcohol, or other cosmetically acceptable materials, which are solid or semi-solid at room temperature and provide a consistency suitable for application to the skin.

Antioxidants may be added to the composition, preferably to act as ingredient protectants and for maintenance of long-term stability of the composition. Examples of antioxidants include, but are not limited to citric acid, butylated hydroxytoluene, pentaerythrityl tetra-di-t-butyl hydroxyhydrocinnamate.

The composition may also contain polymeric materials for thickening, such as polyamides, cellulose derivatives (e.g., hydroxypropylcellulose, hydroxypropyl methyl cellulose, etc.) and natural or synthetic gums, such as polyglycerides including agar, agarose, pectin, or guars or mixtures or combinations thereof. One class of materials worthy of attention for thickening a water-immiscible phase comprises derivatives of hydrolysed starch or other polysaccharides, including in particular esterified dextrins, such as dextrin palmitate. A further class of polymers that is particularly directed to structuring an oil phase containing a silicone oil comprises polysiloxane elastomers. Suspending agents such as silicas or clays such as bentonite, montmorillonite or hectorite, including those available under the trademark Bentone can also be employed to thicken liquid compositions according to the disclosure. The composition can be thickened with non-polymeric organic gellants, including selected dibenzylidene alditols (e.g., dibenzylidene sorbitol).

Fragrance may be included in the personal care composition. Any fragrance suitable for personal care use may be incorporated into the personal care composition of the disclosure. Fragrances tend to be relatively volatile aroma compounds which are capable of entering the gas phase at skin surface temperature.

The personal care compositions of the disclosure may be manufactured using methods known in the art. Typically, the ingredients are combined and optionally heated where components need to be melted. The components are mixed. Desirably, volatile materials such as fragrant materials are incorporated in the composition in the latter stages of a mixing cycle in order to avoid volatilization thereof. After mixing, the composition may be poured directly into the dispensers and the container capped to preserve the product until use.

In another aspect, the disclosure provides a method of depositing a topically active compound on the skin, comprising applying an effective amount of any of personal care compositions disclosed herein, e.g., any of Compositions 1 et seq., to the skin.

In another aspect, the disclosure provides the use of a surfactant system comprising an acyl glutamate, e.g., sodium cocoyl glutamate, in an amount of from 1% to 10% by weight of the composition, e.g., any surfactant system disclosed herein, any of Compositions 1 et seq, in a personal care composition comprising at least one topically active compound, e.g., vitamin, for example vitamin E, for increasing the deposition of the at least one topically active compound on the skin when applying the composition to the skin.

EXAMPLES

To evaluate vitamin E deposition on the skin using rinse off formulations, vitamin E acetate was incorporated into relevant formulation after the formulation was prepared.

Example 1

Basic Sulfate Free Personal Composition
A basic sulfate free personal care formulation, comprising ingredients according to Table 1, was prepared according to methods known in the art.

TABLE 1

Basic Formulation

| Ingredients | Amount [%] |
| --- | --- |
| Surfactants alkyl glucoside (e.g. decyl glucoside, caprylyl/capryl glucoside, lauryl glucoside, coco-glucoside, octyl glucoside, cetearyl glucoside, cetyl glucoside, hexadecyl glucoside, arachidyl glucoside) acyl glutamates, dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate) | 1.00-20.0 |
| Humectants (e.g., glycerin, sorbitol, propylene glycol, polyethylene glycol, xylitol) | 4.0-10.0 |
| Other (antibacterial, pH adjusters, antioxidants, fragrance) (e.g., citric acid, lactic acid, butylated hydroxytoluene, pentaerythrityl tetra-di-t-butyl hydroxyhydrocinnamate,) | 0.05-3.0 |
| Thickeners (e.g., xanthan gum, carrageenan, Irish moss, colloidal silica, fumed silica, cross-linked polyvinylpyrrolidone (PVP) polymers, carboxyvinyl polymers, karaya gum, gum arabic, tragacanth gum, hydroxyethylcellulose, carboxymethylcellulose, colloidal magnesium aluminum silicate) | 0.3-2.0 |
| Oils (e.g., sunflower seed oil, olive oil, shea butter, jojoba oil, almond oil, grape seed oil, rose hip seed oil, mink oil, castor oil, soybean oil, mineral oil) | 0.0-5.0 |
| Water | Q.S. |

Example 2

Determination of the Vitamin E Acetate Deposition
Thirteen basic personal care formulations were prepared according to Table 1, wherein the surfactants and the thickeners were varied. All formulations comprise 7% weight (based on the total weight) of a combination of glycerin, lactic acid and citric acid. Vitamin E acetate, in an amount of 0.1% weight, based on the total weight of the personal care formulation, was added to each of these samples and the pH of the samples was adjusted between 4.5 and 5.5 using lactic acid.

The vitamin E acetate deposition test was performed as follows: deposition studies were conducted on porcine back skin explants. An appropriate amount of formula was applied to the skin, rubbed on, and then rinsed off with warm tap water. The deposition experiments were performed with 50 µL dosing of formula, which approximates actual consumer usage. Deposited actives were extracted off the skin with methanol, and the resulting concentration of vitamin E acetate was quantitatively determined using HPLC with a UV-Vis detector. HPLC analysis was performed using a reverse phase, C18 column and a mobile phase consisting of 99:1 ratio (vol:vol) of methanol:water.

As mentioned above, all deposition tests were run at 0.1% loading of vitamin E acetate. These formulations and deposition results are tabulated in Table 2 and Table 3.

TABLE 2

Formulations 1 to 7

| Ingredient [%] | 1[b] | 2[b] | 3[c] | 4[c] | 5[c] | 6[c] | 7[c] |
|---|---|---|---|---|---|---|---|
| Decyl glucoside | 10 | 2.20 | 10 | 2.20 | 4.10 | 5.60 | 8.10 |
| caprylyl/capryl glucoside | 0 | 0 | 0 | 0 | 0 | 0 | 0 |
| SCG sodium cocoyl glutamate | 0 | 7.80 | 0 | 7.80 | 5.90 | 4.40 | 1.90 |
| Xanthan gum | 1 | 1 | 1 | 1 | 1 | 1 | 1 |
| Carrageenan | 0 | 0 | 0 | 0 | 0 | 0 | 0 |
| Sunflower seed oil | 0 | 0 | 3.40 | 3.40 | 3.40 | 3.40 | 3.40 |
| vitamin E acetate | 0.10 | 0.10 | 0.10 | 0.10 | 0.10 | 0.10 | 0.10 |
| Other[a] | 7 | 7 | 7 | 7 | 7 | 7 | 7 |
| Water | Q.S. | Q.S. | Q.S. | Q.S. | Q.S. | Q.S. | Q.S. |
| Vitamin E Acetate deposition [µg/cm2] | 0.18 ± 0.03 | 0.33 ± 0.12 | 0.10 ± 0.01 | 0.54 ± 0.03 | 0.39 ± 0.06 | 0.24 ± 0.04 | 0.22 ± 0.01 |

[a]glycerin, lactic acid and citric acid
[b]Run separately from Formulations 3-13
[c]Run separately from Formulations 1-2 and 8-13
[d]Run separately from Formulations 1-7 and 11-13
[e]Run separately from Formulations 1-10

TABLE 3

Formulations 8 to 13

| Ingredient [%] | 8[d] | 9[d] | 10[d] | 11[e] | 12[e] | 13[e] |
|---|---|---|---|---|---|---|
| Decyl glucoside | 2.20 | 5.60 | 10 | 0.55 | 1.64 | 2.70 |
| caprylyl/capryl glucoside | 0 | 0 | 0 | 1.64 | 4.90 | 8.20 |
| SCG sodium cocoyl glutamate | 7.80 | 4.40 | 0 | 7.80 | 3.90 | 0 |
| Xanthan gum | 0.70 | 0.70 | 0.70 | 0.70 | 0.70 | 0.70 |
| Carrageenan | 0.30 | 0.30 | 0.30 | 0.30 | 0.30 | 0.30 |
| Sunflower seed oil | 3.40 | 3.40 | 3.40 | 3.40 | 3.40 | 3.40 |
| vitamin E acetate | 0.10 | 0.10 | 0.10 | 0.10 | 0.10 | 0.10 |
| Other[a] | 7 | 7 | 7 | 7 | 7 | 7 |
| Water | Q.S. | Q.S. | Q.S. | Q.S. | Q.S. | Q.S. |
| Vitamin E Acetate deposition [µg/cm2] | 0.57 ± 0.05 | 0.34 ± 0.06 | 0.23 ± 0.01 | 1.22 ± 0.40 | 0.50 ± 0.02 | 0.29 ± 0.12 |

[a]glycerin, lactic acid and citric acid
[b]Run separately from Formulations 4-13
[c]Run separately from Formulations 1-3 and 8-13
[d]Run separately from Formulations 1-7 and 11-13
[e]Run separately from Formulations 1-10

Separately, vitamin E deposition results are obtained from additional formulations containing 10% sodium cocoyl glutamate and which not contain any decyl glucoside nor any caprylyl/capryl glucoside. Formulations 14-17 were separately from formulations 1-13 described in Tables 2 and 3:

TABLE 4

Formulations 14 to 17

| Ingredient [%] | 14 | 15 | 16 | 17 |
|---|---|---|---|---|
| Decyl glucoside | 0 | 0 | 0 | 0 |
| caprylyl/capryl glucoside | 0 | 0 | 0 | 0 |
| SCG sodium cocoyl glutamate | 10 | 10 | 10 | 10 |
| Xanthan gum | 0.70 | 1 | 1 | 0.70 |
| Carrageenan | 0.30 | 0 | 0 | 0.30 |
| Sunflower seed oil | 0 | 0 | 3.40 | 3.40 |
| vitamin E acetate | 0.10 | 0.10 | 0.10 | 0.10 |
| Other[a] | 7 | 7 | 7 | 7 |
| Water | Q.S. | Q.S. | Q.S. | Q.S. |
| Vitamin E Acetate deposition [µg/cm2] | 0.91 ± 0.09 | 1.08 ± 0.46 | 0.75 ± 0.13 | 0.72 ± 0.03 |

[a]glycerin, lactic acid and citric acid

Figure 2:
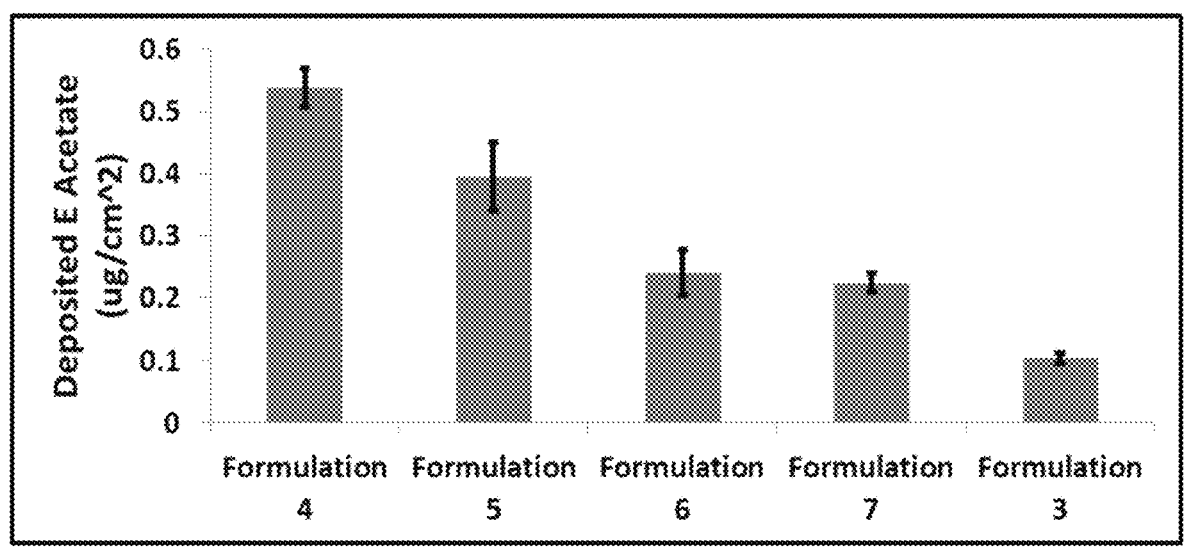
FIG. 2 shows vitamin E acetate deposition of Formulation 4, Formulation 5, Formulation 6, Formulation 7 and Formulation 3.
Figure 3:
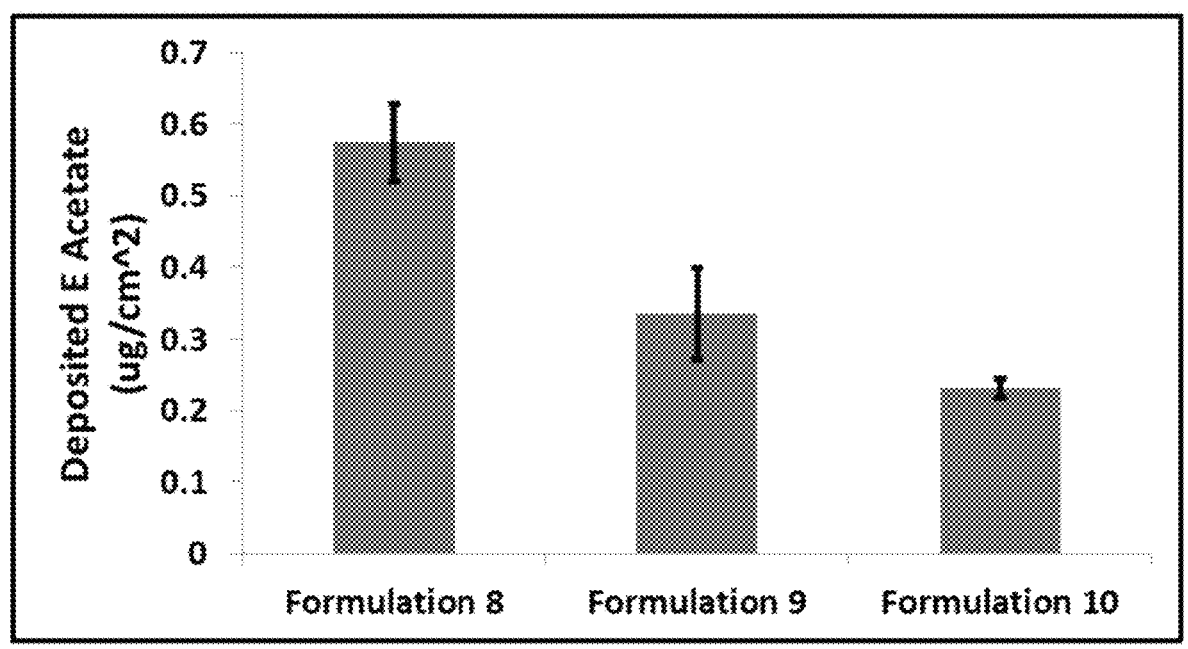
FIG. 3 shows vitamin E acetate deposition of Formulation 8, Formulation 9 and Formulation 10.
Figure 4:
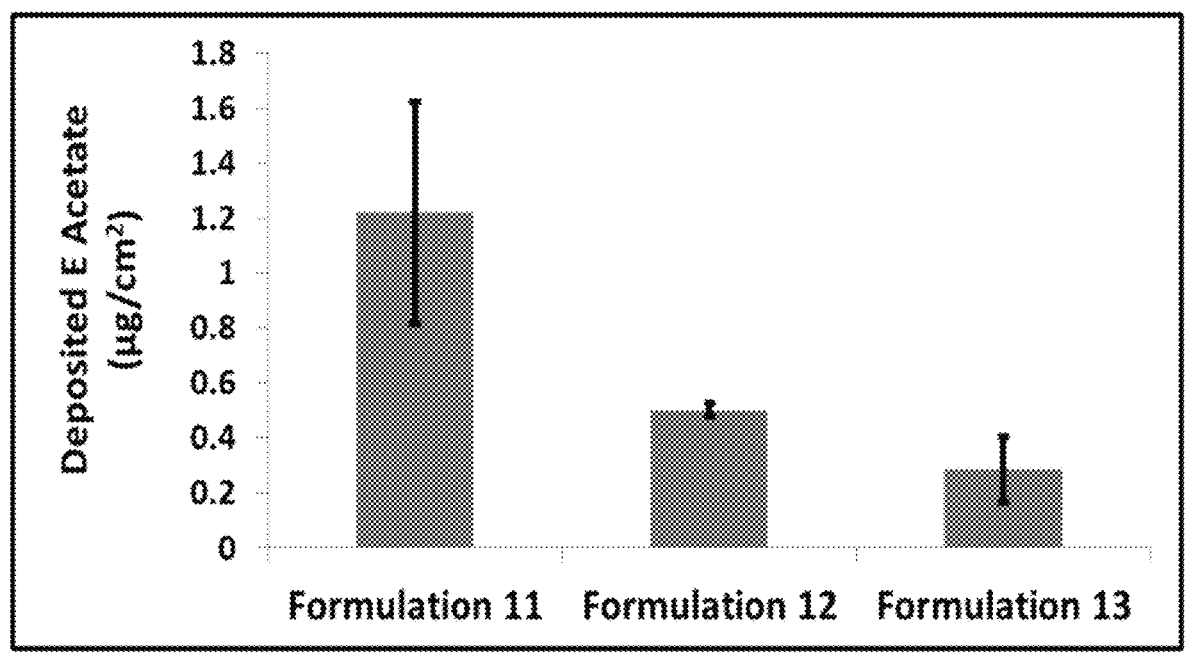
FIG. 4 shows vitamin E acetate deposition of Formulation 11, Formulation 12 and Formulation 13.

The sulfate-free formulations containing SCG show a clear dosing effect on the deposition of vitamin E acetate, with higher levels of vitamin E acetate deposited with increased levels of SCG, as shown in Table 2 and Table 3 and FIGS. 2, 3 and 4.

The deposition properties of Formulations 1 and 2 were compared. SCG is not present in Formulation 1 and is present in Formulation 2. The deposition of vitamin E acetate was about double for Formulation 2 compared to Formulation 1, as shown in FIG. 1.

Formulations 1 and 2 do not include sunflower seed oil and are slightly translucent aqueous gel-like products while Formulations 3 and 4, both with sunflower seed oil, have an off-white appearance. The addition of sunflower seed oil (3.4%) caused the initial formulation to go from a roughly homogenous mixture to oil in water emulsion.

Carrageenan was incorporated as a co-thickener along with xanthan gum. Without being bound by any theory, it could be hypothesized that carrageenan may change the final formulation texture and thus may affect the deposition of actives. Formulations 8, 9, and 10 increase in the deposition of vitamin E acetate was observed with the lowest level of vitamin E acetate deposition coming from Formulation 10, no SCG content, as shown in FIG. 3.

Formulations 11, 12 and 13 comprise a surfactant system containing decyl glycoside and caprylyl/capryl glucoside and various amounts of SCG. The total surfactant amount remained constant at roughly 10% and the ratio of caprylyl/capryl glucoside to decyl glucoside also remained constant at roughly 3:1. A clear dose-dependent increase in the deposition of vitamin E acetate was observed, with the lowest level of vitamin E acetate deposition coming from the Formulation 13, no SCG content, as shown in FIG. 4.

Formulations 14, 15, 16 and 17 comprise a surfactant system containing 10% SCG and no decyl glycoside or caprylyl/capryl glucoside. The total surfactant amount remained at 10%.

These results show that the addition of SCG into sulfate-free rinse off formulas leads to a significant increase in vitamin E acetate deposition.

The present disclosure has been described with reference to exemplary embodiments. Although a limited number of embodiments have been shown and described, it will be appreciated by those skilled in the art that changes may be made in these embodiments without departing from the principles and spirit of the preceding detailed description. It is intended that the present disclosure be construed as including all such modifications and alterations insofar as they come within the scope of the appended claims or the equivalents thereof.

The invention claimed is:

1. A personal care composition comprising:
an acyl glutamate in an amount of from 1% to 10% by weight of the composition; and at least one topically active compound, wherein the at least one topically active compound comprises vitamin E in an amount of from 0.05% to 1% by weight of the composition;
wherein the composition further comprises co-surfactant comprising an alkyl glucoside;
wherein the alkyl glucoside is a combination of decyl glucoside and caprylyl/capryl glucoside;
wherein the weight ratio of caprylyl/capryl glucoside to decyl glucoside is from 2:1 to 4:1; and
wherein the total amount of surfactants present in the composition is from 8% to 12% by weight of the composition.

2. The composition of claim 1, wherein the acyl glutamate is $C_{8-25}$ acyl glutamate.

3. The composition of claim 1, wherein the acyl glutamate is sodium cocoyl glutamate.

4. The composition of claim 1, wherein the acyl glutamate is present in an amount of from 2% to 8% by weight of the composition.

5. The composition of claim 1, wherein the alkyl glucoside is present in an amount of from 2% to 8% by weight of the composition.

6. The composition of claim 1, wherein the composition further comprises a vitamin selected from vitamin C, vitamin D, vitamin K, or a combination thereof.

7. The composition of claim 1, wherein the composition further comprises an oil, wherein the oil is selected from sunflower seed oil, olive oil, shea butter, jojoba oil, almond oil, grape seed oil, rose hip seed oil, mink oil, castor oil, soybean oil, mineral oil, or a combination thereof.

8. The composition of claim 1, wherein the composition further comprises a thickener.

9. The composition of claim 8, wherein the thickener comprises a gum.

10. The composition of claim 9, wherein the gum is selected from xanthan gum, carrageenan, or a combination thereof.

11. The composition of claim 1, wherein the composition further comprises a humectant selected from glycerin, sorbitol, or a mixture thereof.

12. The composition of claim 1, wherein the composition is free or substantially free of sodium lauryl sulfate (SLS).

13. The composition of claim 1, wherein the composition is a rinse off composition, and wherein the rinse off composition is a liquid soap, liquid hand soap, shower gel, body wash, shampoo, or hair conditioner.

14. A method of depositing a topically active compound on the skin, comprising applying an effective amount of the personal care composition of claim 1.

15. The personal care composition of claim 1, wherein the weight ratio of caprylyl/capryl glucoside to decyl glucoside is 3:1.

* * * * *